(12) United States Patent
Warner et al.

(10) Patent No.: US 10,527,600 B2
(45) Date of Patent: Jan. 7, 2020

(54) SENSORS AND SENSOR ARRAYS FOR DETECTION OF ANALYTES

(71) Applicant: Icagen, Inc., Durham, NC (US)

(72) Inventors: Benjamin P. Warner, Durham, NC (US); Chang-Tai Hsieh, Durham, NC (US); Emilia Solomon, Durham, NC (US); Lori Peterson, Durham, NC (US); Douglas Krafte, Durham, NC (US); Nathan Zahler, Durham, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 16/094,399

(22) PCT Filed: Apr. 18, 2017

(86) PCT No.: PCT/US2017/028064
§ 371 (c)(1),
(2) Date: Oct. 17, 2018

(87) PCT Pub. No.: WO2017/184564
PCT Pub. Date: Oct. 26, 2017

(65) Prior Publication Data
US 2019/0120807 A1    Apr. 25, 2019

Related U.S. Application Data

(60) Provisional application No. 62/341,403, filed on May 25, 2016, provisional application No. 62/337,551, (Continued)

(51) Int. Cl.
*G01N 33/00* (2006.01)
*G01N 33/18* (2006.01)
*G01N 23/223* (2006.01)

(52) U.S. Cl.
CPC ......... *G01N 33/182* (2013.01); *G01N 23/223* (2013.01); *G01N 33/1813* (2013.01); *G01N 2223/076* (2013.01)

(58) Field of Classification Search
CPC .................................................. G01N 33/182
(Continued)

(56) References Cited

U.S. PATENT DOCUMENTS 3,953,599 A    4/1976 MacMillan et al.
4,577,337 A    3/1986 Light
(Continued)

OTHER PUBLICATIONS

Aoki, et al., "Imaging X-ray fluorescence microscope with a Wolter-type grazing-incidence mirror," J. Synchrotron Rad., 5: 1117-1118 (1998).

(Continued)

*Primary Examiner* — Christine T Mui
*Assistant Examiner* — Emily R. Berkeley
(74) *Attorney, Agent, or Firm* — Morgan, Lewis & Bockius LLP

(57) ABSTRACT

Methods, apparatus and compositions are described for the measurement of metal and/or metalloid elements, including selenium in samples. More specifically, the invention provides a sensor and/or array of sensors to measure metal and/or metalloid analytes, e.g. sensor and/or array of sensors having a chelator molecule, the chelator molecule including a peptide which has a phenylalanine derivative.

5 Claims, 3 Drawing Sheets

Specification includes a Sequence Listing.

Related U.S. Application Data filed on May 17, 2016, provisional application No. 62/324,057, filed on Apr. 18, 2016.

(58) Field of Classification Search
USPC .................................................. 422/68.1
See application file for complete search history.

(56) References Cited

U.S. PATENT DOCUMENTS

| | | |
|---|---|---|
| 4,717,826 A | 1/1988 | Silver |
| 5,574,284 A | 11/1996 | Farr |
| 5,778,039 A | 7/1998 | Hossain et al. |
| 6,858,148 B2 | 2/2005 | Warner et al. |
| 7,241,381 B2 | 7/2007 | Warner et al. |
| 7,519,145 B2 | 4/2009 | Warner et al. |
| 7,545,910 B2 | 6/2009 | Harding et al. |
| 7,688,943 B2 | 3/2010 | Chikawa |
| 7,858,385 B2 | 12/2010 | Warner et al. |
| 7,929,662 B2 | 4/2011 | Warner et al. |
| 8,238,515 B2 | 8/2012 | Birnbaum et al. |
| 8,263,410 B2 | 9/2012 | Kang et al. |
| 8,431,357 B2 | 4/2013 | Birnbaum et al. |
| 8,873,707 B2 | 10/2014 | Birnbaum et al. |
| 9,052,319 B2 | 6/2015 | Simon et al. |
| 9,063,066 B2 | 6/2015 | Peterson et al. |
| 9,063,154 B2 | 6/2015 | Warner et al. |
| 9,157,875 B2 | 10/2015 | Warner et al. |
| 9,335,284 B2 | 5/2016 | Peterson et al. |
| 9,435,756 B2 | 9/2016 | Peterson et al. |
| 9,442,085 B2 | 9/2016 | Peterson et al. |
| 9,476,846 B2 | 10/2016 | Birnbaum et al. |
| 9,506,931 B2 | 11/2016 | Warner et al. |
| 9,976,172 B2 | 5/2018 | Birnbaum et al. |
| 10,082,474 B2 | 9/2018 | Peterson et al. |
| 10,082,511 B2 | 9/2018 | Warner et al. |
| 2004/0235059 A1 | 11/2004 | Warner et al. |
| 2007/0258561 A1 | 11/2007 | Chikawa |
| 2008/0090304 A1 | 4/2008 | Barasch et al. |
| 2008/0220441 A1 | 9/2008 | Birnbaum et al. |
| 2009/0087919 A1 | 4/2009 | Birnbaum et al. |
| 2010/0021887 A1 | 1/2010 | Azoulay et al. |
| 2010/0299766 A1 | 11/2010 | Demuth et al. |
| 2010/0312072 A1 | 12/2010 | Breskin et al. |
| 2011/0046204 A1 | 2/2011 | Costello et al. |
| 2011/0052447 A1 | 3/2011 | Roy et al. |
| 2012/0093286 A1 | 4/2012 | Peterson et al. |
| 2012/0282648 A1 | 11/2012 | Simon et al. |
| 2013/0330276 A1 | 12/2013 | Caviglioli et al. |
| 2014/0107043 A1* | 4/2014 | Baleux ............ C07K 14/70514 514/21.3 |
| 2015/0260664 A1 | 9/2015 | Peterson et al. |
| 2015/0276631 A1 | 10/2015 | Peterson et al. |
| 2015/0276632 A1 | 10/2015 | Peterson et al. |
| 2016/0341678 A1 | 11/2016 | Peterson et al. |
| 2018/0100866 A9 | 4/2018 | Barasch et al. |
| 2019/0011382 A1 | 1/2019 | Peterson et al. |

OTHER PUBLICATIONS

Ohtsuki, "How to prepare the simulated body fluid (SBF) and its related solutions, proposed by Kokubo and his colleagues." Accessed online Apr. 14, 2015.

Carter, Kyle P. et al., "Fluorescent sensors for measuring metal ions in living systems," Chemical Reviews, 2014, vol. 114, pp. 4564-4601.

Neupane, Lok Nath et al., "Selective and sensitive detection of heavy metal ions in 100% aqueous solution and cells with a fluorescence chemosensor based on peptide using aggregation-induced emission", Analytical Chemistry, Epub. Feb. 12, 2016, vol. 88, No. 6, pp. 3333-3340.

Pazos, Elena et al., "Peptide-based fluorescent biosensors", Chemical Society Reviews, 2009, vol. 38, pp. 3348-3359.

Written Opinion, PCT Appl. No. PCT/US2017/028064, dated Jul. 11, 2017, 7 pages.

* cited by examiner

SENSORS AND SENSOR ARRAYS FOR DETECTION OF ANALYTES

CROSS-REFERENCE TO RELATED APPLICATIONS

This application is a 371 national stage entry of PCT/US2017/028064, filed on Apr. 18, 2017, which claims the benefit of U.S. Provisional Patent Application Nos. 62/324,057, filed Apr. 18, 2016; 62/337,551, filed May 17, 2016; and 62/341,403, filed May 25, 2016; the entire contents of all of which are herein incorporated by reference.

FIELD

The presently described inventions relate, in part, to sensors and arrays of sensors, as well as methods, compositions and apparatuses, for measuring metals and/or metalloids. More specifically the inventions include, for example, measuring selenium in environmental water or biological samples.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ICA-010PC_Sequence_listing; date recorded: Apr. 18, 2017; file size: 4.49 KB).

BACKGROUND

Elemental analysis, which generally refers to the process by which a sample (e.g., soil, waste or drinking water, bodily fluids, minerals, etc.) is analyzed for its elemental composition is central to a variety of analytical techniques that find use in, for example, environmental and medical applications.

Many metals or metalloids, for example, play important roles in physiological processes. The human body is exposed to various elemental forms of these metals or metalloids which are ubiquitous in animals, plants, rocks, soil, water, and air. Exposure to these metals or metalloids can be from air inhalation, food and water intake, surgical implants, and occupational scenarios, among others.

Selenium, a metalloid, is among the rarest elements on the surface of the planet and it is released through both natural and human activities. For example, exposure of selenium containing minerals to air and water can mobilize selenium by forming soluble ions such as selenate ($SeO_4^{2-}$) and selenite ($SeO_3^{2-}$). Solubility increases as the pH decreases. Mining activities, such as the refining of metal sulfide ores is one source of mobilized selenium. Selenium is also found in coal in small amounts but when coal-bearing strata are exposed to air and water during the mining process the selenium is mobilized and forms contaminated leachate, which often becomes a source of pollution to nearby surface waters. Coal and other fossil fuel combustion also release selenium to the environment. Well fertilized agricultural soil has about 400 mg/ton of selenium since the element is present in phosphate fertilizer.

Elemental forms of selenium include various valence or oxidation states. This speciation can be important because the differing valence states can have different chemical properties. Common selenium valence states include hexavalent selenium and tetravalent selenium. Also, elemental forms include metals in various valence states. This speciation can be important because the differing valence states can have contrasting physiological effects.

Selenium can be toxic in large amounts, and selenium is often measured in wastewater to ensure that it is present within acceptable concentrations. There are currently few selective, sensitive, specific, and inexpensive assays for metals and/or metalloids, inclusive of selenium, and various species thereof. Additionally, there are currently few assays that differentiate metal and/or metalloid species, for instance selenium species, by oxidation state. Further, the current technology cannot provide real time detection of selenium quickly. For instance, existing methodology such as ICP-MS is effective at measurement, but do not have acceptable throughput and turn-around time to allow responses to mitigate waste stream contamination to occur in an acceptable time frame.

There remains a need for new and improved sensors and arrays of sensors for measuring metals and/or metalloids.

SUMMARY

Accordingly, in general, methods, compositions and apparatuses are disclosed herein for the analysis and determination of various metal and/or metalloid elements, such as selenium. For example, various metal and/or metalloid elements, such as selenium can be selectively detected in a complex sample including other elements.

In various aspects, the invention provides a sensor and/or array of sensors to measure metal and/or metalloid analytes (e.g. selenium).

In various aspects, the invention provides a sensor and/or array of sensors to measure metal and/or metalloid analytes (e.g. selenium) comprising more than one chelator molecule and a solid support, which are optionally attached to each other. In some embodiments, the chelator molecule is a peptide, small molecule, or cationic or anionic polymer that is able to bind to a metal and/or metalloid analyte (e.g. selenium). In some embodiments, the solid support is glass or polymer surface.

In some aspects, the invention provides a sensor and/or array of sensors to measure metal and/or metalloid analytes (e.g. selenium) using various chelator molecules capable of concentrating the metal and/or metalloid analytes (e.g. selenium) from the sample (e.g. solution, including waste water streams from power plants and other industrial sources).

In some embodiments, the present sensors and/or arrays of sensors comprise one or more sensors where the sensors that have an ability to bind and detect a metal and/or metalloid analyte of interest. In various embodiments, the present sensors and/or arrays of sensors comprise one or more sensors that have an ability to bind and detect a metal and/or metalloid analyte of interest and the one or more sensors have different affinities for the metal and/or metalloid analyte of interest. For instance, coupling multiple sensors together which have differing affinities for the same analyte allows a range of concentrations to be detected. In various embodiments, the present array allows one to detect analyte in real time, despite, depending on affinity, one or more individual sensors saturating. The present arrays, without wishing to be bound by theory, overcome this saturation issue by providing sensors that can detect across a range of analyte concentrations. In various embodiments, the array of sensors comprises one or more sensors that have an ability to bind and detect selenium and one or more sensors have different affinities for selenium.

In some embodiments, the present sensors and/or arrays of sensors comprise one or more sensors where the sensors that have an ability to bind and detect a different species of a single metal and/or metalloid analyte of interest, inclusive of detection at different concentrations. For instance, in some embodiments, the present sensors and/or arrays of sensors comprise one or more sensors where the sensors that have an ability to bind and detect selenium species selenate and/or selenite.

In some embodiments, the present sensors and/or arrays of sensors comprise one or more sensors that have an ability to bind and detect different metal and/or metalloid analytes of interest, inclusive at different concentrations. For example, in various embodiments, the present sensors and/or arrays of sensors comprise a sensor for selenium and another element.

In some embodiments, the present sensors and/or arrays of sensors allow for multiplexed detection of more than one different metal and/or metalloid analyte of interest, or various forms or species thereof, and various ranges of concentrations of the different metal and/or metalloid analyte of interest.

In some aspects, the invention provides a method for measuring selenium, inclusive of, for example, selenate and/or selenite, in a sample, for example a liquid sample. Such method includes, in various embodiments, contacting (e.g., combining) a solution containing selenium and sensor as described herein, e.g. comprising a resin capable of concentrating the selenium from the sample (e.g. solution). In various embodiments, the method also includes measuring a sample of the selenium that is concentrated on the sensor as described herein, e.g. comprising a resin. The measurement can be, for example, an elemental analysis method. For example the elemental analysis may be one or more of x-ray fluorescence, atomic absorption spectroscopy, atomic emission spectroscopy, mass spectrometry, and laser induced breakdown spectroscopy. In various embodiments, the measurement allows for differentiation among species of selenium, inclusive of, for example, selenate and/or selenite.

In various embodiments, the solid support of the present invention is capable of concentrating a metal and/or metalloid element from the sample (e.g. solution). In an embodiment of the method, the solid support comprises a chelator molecule, such as a peptide.

In various embodiments, the present sensors and/or arrays of sensors are suitable for measurement using, for example, an elemental analysis method. For example the elemental analysis may be one or more of x-ray fluorescence, atomic absorption spectroscopy, atomic emission spectroscopy, mass spectrometry, and laser induced breakdown spectroscopy.

In some aspects, the invention provides a method for measuring a metal and/or metalloid analyte of interest including selenium. Such measurement may allow differentiation of concentrations of the metal and/or metalloid analyte of interest and/or identification of different metal and/or metalloid analytes of interest in the same sample. In some embodiments, the metal and/or metalloid analyte of interest is selenium, inclusive of selenate and/or selenite. Such method includes, in various embodiments, contacting (e.g., combining) a solution containing a metal and/or metalloid analyte of interest, inclusive, without limitation of selenium, and the present sensors and/or arrays of sensors. In various embodiments, the method also includes measuring a sample of the selenium that is concentrated on the present sensors and/or arrays of sensors. The measurement can be, for example, an elemental analysis method. For example the elemental analysis may be one or more of x-ray fluorescence, atomic absorption spectroscopy, atomic emission spectroscopy, mass spectrometry, and laser induced breakdown spectroscopy. In various embodiments, the measurement allows for differentiation among different metal and/or metalloid analytes of interest in the same sample. In various embodiments, the measurement allows for differentiation among species of selenium, inclusive of, for example, selenate and/or selenite.

Such methods find use in a variety of applications described herein, including, without limitation, environmental analysis for pollution (e.g. air, water) and/or occupational exposure and/or medical applications. In various embodiments, the present methods find use in monitoring waste stream analyte levels, e.g. in effluent from power plants, mining and refining operations or any other industrial process where measurement and detection of certain analytes is required or desired.

Furthermore, in some embodiments, the x-ray excitation source is disposed to excite the resin and the x-ray detector is disposed to measure x-rays emitted from the sensor (e.g. comprising a resin). In some embodiments the x-ray detector is an energy dispersive x-ray detector. Alternatively or additionally the x-ray excitation source utilizes polychromatic x-rays for exciting the sample. Alternatively or additionally the x-ray excitation source utilizes a micro-focus x-ray tube. In some embodiments the x-ray excitation source utilizes a focusing optic. An embodiment of the present apparatus is found in FIG. 1.

Other features and advantages of the invention will be apparent from the following detailed description, drawings, and from the claims.

DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

FIG. 2 shows a solid support or resin (I) with covalently attached chelators (e.g. peptides, II). In the non-limiting embodiments shown in FIG. 2, each sensor binds a target analyte with varying affinities, leading to overlapping response curves (e.g.

FIG. 3 is an illustrative graph showing the differential binding/signal generation effect of the sensors and/or arrays of sensors of various embodiments of the present invention. The varying affinities allow for quantitative measurements over a dynamic range not provided the response of a single affinity sensor.

DETAILED DESCRIPTION

Figure 1:
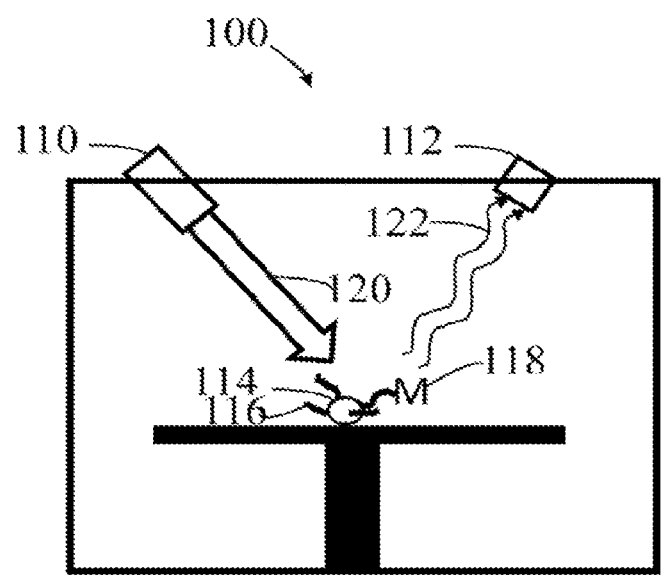
FIG. 1 shows an apparatus for measuring the x-ray fluorescence emitted from sensors and/or arrays of sensors as provided in an embodiment described herein.

The sensors and/or arrays of sensors described herein, and methods, apparatuses, and compositions described herein, can provide selective, sensitive, specific, and inexpensive assays for various elements. For instance, the methods, apparatuses and compositions described herein can provide selective, sensitive, specific, and inexpensive assays for selenium, e.g. selenate and/or selenite, exposures.

In various embodiments, the present invention provides for the detection of metal and/or metalloid elements. For example, detection of selenium is provided in some embodiments. Particular embodiments relate to the selective detection of metals and/or metalloids, such as selenium, over dynamic ranges that are suited for real time sampling and measurement. Particular embodiments relate to the selective detection of metals and/or metalloids, such as selenium, in specific oxidation states. Detection can be by any useful means and include detection using a solid support or resin to concentrate the metal and/or metalloid and x-ray fluorescence spectroscopy.

Sensors and/or Arrays of Sensors

In various embodiments, the sensors and/or arrays of sensors of the present invention comprise more than one sensors for detection, e.g. 2, or 3, or 4, or 5, or 6, or 7, or 8, or 9, or 10 sensors.

In various embodiments, the sensors and/or arrays of sensors of the present invention comprise sensors that bind to a metal and/or metalloid analyte of interest at different affinities from each other. For instance, in some embodiments, more than one sensor that binds to a metal and/or metalloid analyte of interest is provided and the various sensors have affinities for the metal and/or metalloid analyte of interest that differ from each other by about 3-, or 5-, or 10-, or 30-, or 50-, or 100-fold. For example, in one embodiment, at least two sensors are provided, the sensors having about a 10-fold difference in affinity for the metal and/or metalloid analyte of interest. For example, in another embodiment, at least three sensors are provided, the sensors each having about a 10-fold difference in affinity for the metal and/or metalloid analyte of interest from each other.

In various embodiments, the sensors and/or arrays of sensors of the present invention comprise sensors that bind to selenium at different affinities from each other. For instance, in some embodiments, more than one sensor that binds to selenium is provided and the various sensors have affinities for selenium that differ from each other by about 3-, or 5-, or 10-, or 30-, or 50-, or 100-fold. For example, in one embodiment, at least two sensors are provided, the sensors having about a 10-fold difference in affinity for selenium.

In various embodiments, the sensors and/or arrays of sensors of the present invention comprise sensors that bind to a metal and/or metalloid analyte of interest at different affinities from each other but for which the concentration response profiles are overlapping.

In various embodiments, the sensors and/or arrays of sensors have differing affinity for an analyte of interest and this provides increased and/or extended sensitivity, dynamic range and selectivity of measurements, e.g. X-ray fluorescence measurements than, for instance, single affinity sensors.

In various embodiments, detection limits are extended through the use of high-affinity sensors. In various embodiments, linear range is extended through the use of multiple sensors with overlapping response ranges.

In various embodiments, the sensors and/or arrays of sensors of the present invention comprise sensors that bind to a different, additional metal and/or metalloid analytes of interest, and optionally the sensors for each of the metal and/or metalloid analytes of interest have different affinities from each other. In some embodiments, the sensors and/or arrays of sensors bind selenium, optionally with different affinities among the selenium sensors, and another analyte, optionally with different affinities among the other analyte sensors. Illustrative other analytes include Lithium, Beryllium, Boron, Sodium, Magnesium, Aluminum, Silicon, Potassium, Calcium, Scandium, Titanium, Vanadium, Chromium, Manganese, Iron, Cobalt, Nickel, Copper, Zinc, Gallium, Germanium, Arsenic, Rubidium, Strontium, Yttrium, Zirconium, Niobium, Molybdenum, Technetium, Ruthenium, Rhodium, Palladium, Silver, Cadmium, Indium, Tin, Antimony, Tellurium, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Ununtrium, Flerovium, Ununpentium, and Livermorium.

In various embodiments, the sensors and/or arrays of sensors of the present invention comprise sensors that bind to a different metal and/or metalloid analytes of interest (e.g. the sensors and/or arrays of sensors bind to 2, or 3, or 4, or 5, or 10 metal and/or metalloid analytes of interest). In various embodiments, the different metal and/or metalloid analyte of interest is known to compete with the primary metal and/or metalloid analyte of interest for binding to sensors for the primary metal and/or metalloid analyte of interest.

In various embodiments, the sensors and/or arrays of sensors of the present invention comprise sensors that bind to different species of a metal and/or metalloid analytes of interest optionally with different affinities among the metal and/or metalloid analyte sensors. For instance, the present sensors may bind to different oxidation state species of the analyte. For example, the present sensors and/or arrays of sensors, in some embodiments, can detect selenate and/or selenite and optionally have sensors of varying affinities for these species. For instance, the present sensors and/or arrays of sensors may bind different species of one or more of Lithium, Beryllium, Boron, Sodium, Magnesium, Aluminum, Silicon, Potassium, Calcium, Scandium, Titanium, Vanadium, Chromium, Manganese, Iron, Cobalt, Nickel, Copper, Zinc, Gallium, Germanium, Arsenic, Rubidium, Strontium, Yttrium, Zirconium, Niobium, Molybdenum, Technetium, Ruthenium, Rhodium, Palladium, Silver, Cadmium, Indium, Tin, Antimony, Tellurium, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Ununtrium, Flerovium, Ununpentium, and Livermorium and optionally have sensors of varying affinities for these species.

In various embodiments, the sensors and/or arrays of sensors of the present invention comprise sensors that bind to a metal and/or metalloid analyte of interest at different affinities and/or bind to a different metal and/or metalloid analytes of interest and/or bind to different species of a metal and/or metalloid analyte of interest.

In various aspects, the invention provides a sensor and/or array of sensors to measure metal and/or metalloid analytes (e.g. selenium) comprising more than one chelator molecule and a solid support, which are optionally attached to each other. In some embodiments, the chelator molecule is a peptide, small molecule, or cationic or anionic polymer that is able to bind to a metal and/or metalloid analyte (e.g. selenium). In some embodiments, the solid support is glass or polymer surface.

In various embodiments, the sensors and/or arrays of sensors described herein use and/or comprise a solid support, e.g. resin, which may be in the form of a particle. In various embodiments, the resin may comprise a chelator molecule, which is capable of interacting (e.g. binding) a metal and/or metalloid.

Some aspects of the invention relate to a composition that comprises the sensors and/or arrays of sensors, which may optionally further comprise a chelator molecule, e.g. peptide-based ligand and/or metal and/or metalloid.

In some embodiments, the chelator molecule, inclusive of peptide-based ligands, can be bound to a surface, such as the surface of a solid support. The surface can be an interior or exterior surface of a particle. For example, a highly porous particle can have a high percentage of surface area in the particle. For a porous particle, the interior surface area is preferably accessible to metal and/or metalloid ions, therefore having an average pore diameter of at least about 1 nm or larger than about 10 nm (e.g. about 1 nm, or about 5 nm, or about 10 nm, or about 25 nm, or about 50 nm, or about 75 nm, or about 100 nm, or about 200 nm, or about 300 nm, or about 500 nm). The particles can be of any shape such as an approximate sphere, lozenge, cube, cylinder, fiber, cone, prism, or even an irregularly shaped particle can be used.

In some embodiments, the solid support is glass or polymer surface. In various embodiments, the solid support is a resin. In various embodiments, the resin (or "RESIN" as used herein) is one or more materials described immediately below, e.g. as components of particles. The particles can be made using inorganic materials (e.g., silicates, aluminosilicates and siloxanes), organic materials (e.g., polystyrene) or combinations of these. Some particles include polystyrene (PS) resin with some (e.g., 1-2% divinylbenzene) cross linking, also known as Merrifield resin. Other particles include combinations of polyethylene glycol (PEG) and PS such as PEG grafted on a core of PS, for example, TENTAGEL (Bayer Healthcare, Whippany, N.J.) and HYPOGEL (Rapp Polymere GmbH, Tuebingen, Germany), ARGOGEL (Argonaut Technologies Inc., Redwood City, Calif.), and CHAMPION I and II (Biosearch Technologies Inc., Petaluma, Calif.). Another particle is beaded Poly[acryloyl-bis (aminopropyl)polyethylene glycol] commonly known as PEGA resins. Other illustrative particles include polystyrene cross linked with tetra(ethylene glycol) diacrylate (TTEGDA), cross liked ethoxylated acrylate resin such as CLEAR (Peptides International Inc., Louisville, Ky.), poly-ethylene glycol based resins such as CHEMMATRIX (PCAS BioMatrix Inc., Quebec, Canada).

In various embodiments, the RESIN is $PEG_n$-polystyrene, where n is 1-10, e.g. 1, 2, 3, 4, 5, 6, 7, 8, 9, and 10 (e.g. a TENTAGEL resin).

In some embodiments, the chelator molecule is a peptide, small molecule, or cationic or anionic polymer that is able to bind to a metal and/or metalloid analyte (e.g. selenium).

In various embodiments, the chelator molecule is a peptide-based ligand. For instance, the peptide may be associated with, e.g. bound to, a solid support, e.g. resin, as described herein.

In various embodiments, the peptide has a general formula of:

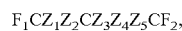

wherein, $F_1$ and $F_2$ are each independently a phenylalanine derivative at position four, as follows:

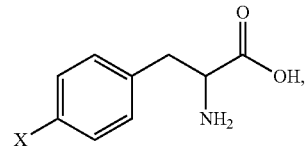

where X is any element. In some embodiments, X is a halogen. In some embodiments, X is one or more of F, Cl, Br, I and At. In some embodiments, the phenylalanine derivative is 4-bromophenylalanine (F4Br) or 4-iodophenylalanine (F4I), and $Z_1$, $Z_2$, $Z_3$, $Z_4$, and $Z_5$ are each independently an amino acid, optionally selected from D, I, P, N, H, Q, R, E, W, S, A, G, F, T, L, V, or modifications thereof.

In some embodiments, the peptide is selected from F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), F4ICDICPNHC (SEQ ID NO: 6), F4ICQRCERWC (SEQ ID NO: 7), F4ICHTCFQTC (SEQ ID NO: 8), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. As used herein, "F4Br" is 4-bromophenylalanine, "F4I" is 4-iodophenylalanine, "YBr" is 3,5-dibromotyrosine, and "YmI" is mono-iodo tyrosine.

In some embodiments, the peptide binds selenate and has a sequence selected from selected from F4ICDICPNHCF4Br (SEQ ID NO: 1), F4ICQRCERWCF4Br (SEQ ID NO: 2), F4ICFHCFSECF4Br (SEQ ID NO: 3), or variants thereof.

In various embodiments, the peptide has a general formula of

wherein: $X_1$ is Q or T and $Y_1$ is a tyrosine derivative at the three and five positions of the structure:

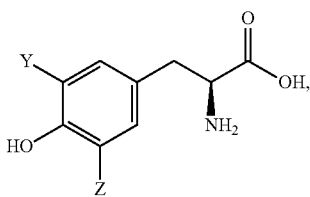

and

Y and Z are a halogen or one or Y and Z is a halogen and one of Y and Z is hydrogen.

In various embodiments, $Y_1$ is 3,5-dibromotyrosine or mono-iodo-tyrosine.

In various embodiments, the peptide comprises one or more of YBrCRTSC (SEQ ID NO: 10), YBrCRQSC (SEQ ID NO: 11), YmICRTSC (SEQ ID NO: 13), and YmICRQSC (SEQ ID NO: 14).

In some embodiments, the peptide binds selenite and has a sequence selected from F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)) and YmICR(T/Q)SC (SEQ ID NO: 12) (e.g. YmICRTSC (SEQ ID NO: 13), YmICRQSC (SEQ ID NO: 14)), or variants thereof.

In some embodiments, the sensor and/or array of sensors comprises a peptide and has a structure selected from F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), F4ICDICPNHC-RESIN (SEQ ID NO: 6-RESIN), F4ICQRCERWC-RESIN (SEQ ID NO: 7-RESIN), F4ICHTCFQTC-RESIN (SEQ ID NO: 8-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)), and YmICR(T/Q)SC-RESIN (SEQ ID NO: 12-RESIN) (e.g. YmICRTSC-RESIN (SEQ ID NO: 12-RESIN), YmICRQSC-RESIN (SEQ ID NO: 13-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)), and RESIN-YmICR(T/Q)SC (RESIN-SEQ ID NO: 12) (e.g. RESIN YmICRTSC (RESIN-SEQ ID NO: 13), RESIN-YmICRQSC (RESIN-SEQ ID NO: 14)). In various embodiments the RESIN is $PEG_n$-polystyrene, where n is 1-10, e.g. 1, 2, 3, 4, 5, 6, 7, 8, 9, and 10 (e.g. a TENTAGEL resin).

In some embodiments, the solution comprises selenate and the sensor and/or array of sensors has a structure selected from F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), or variants thereof.

In some embodiments, the solution comprises selenite and the sensor and/or array of sensors has a structure selected F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)), and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or variants thereof.

In some embodiments, the invention provides for variants of the sequences listed. In some embodiments, the variants are functionally comparable variants.

For example, the present peptides may comprise alterations that do not substantially affect suitability for the uses described herein. For example, one, or two, or three, or four, or five amino acids may be mutated. In some embodiments, the mutation is a substitution. In some embodiments, the mutation is a deletion. In some embodiments, the mutation is an addition. Illustrative mutations are substitutions or additions, which can be conservative or non-conservative in nature.

Conservative substitutions may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. Conservative substitutions may be as exchanges of an amino acid by another amino acid listed within the same group of the six standard amino acid groups shown above. For example, glycine and proline may be substituted for one another based on their ability to disrupt α-helices.

Non-conservative substitutions may be exchanges of an amino acid by another amino acid listed in a different group of the six standard amino acid groups (1) to (6) shown above.

In some embodiments, the peptide comprises at least one non-classical amino acid. Illustrative non-classical amino acids include selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Further, in various embodiments mutations, inclusive of substitutions and additions, may also include non-classical amino acids as described herein.

In some embodiments, the peptide comprises a non-classical amino acid which is a phenylalanine derivative at the four position, as follows:

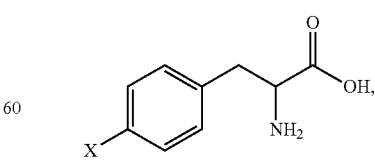

where X is any element. In some embodiments, X is a halogen. In some embodiments, X is one or more of F, Cl, Br, I and At. In some embodiments, the non-classical amino acid is 4-bromophenylalanine and/or 4-iodophenylalanine.

In specific embodiments, the phenylalanine derivative precedes and/or succeeds the following sequences: CDICPNHC, CQRCERWC, CFHCFSEC, CAGCFTGC, and CQLCNVLC.

In some embodiments, the peptide is one or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), F4ICDICPNHC (SEQ ID NO: 6), F4ICQRCERWC (SEQ ID NO: 7), F4ICHTCFQTC (SEQ ID NO: 8), or variants thereof and the F4Br may be substituted for 4-iodophenylalanine (F4I), 4-chlorophenylalanine (F4Cl), or 4-fluorophenylalanine (F4F). In some embodiments, the peptide is one or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), or variants thereof and the F4I may be substituted for 4-fluorophenylalanine (F4F), 4-chlorophenylalanine (F4Cl), or 4-bromophenylalanine (F4Br). In some embodiments, the peptide is one or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), or variants thereof and the F4Br may be substituted for 4-iodophenylalanine (F4I), 4-chlorophenylalanine (F4Cl), or 4-fluorophenylalanine (F4F) and the F4I may be substituted for 4-fluorophenylalanine (F4F), 4-chlorophenylalanine (F4Cl), or 4-bromophenylalanine (F4Br).

In some embodiments, the peptide comprises a non-classical amino acid which is a tyrosine derivative at the three and five positions, as follows:

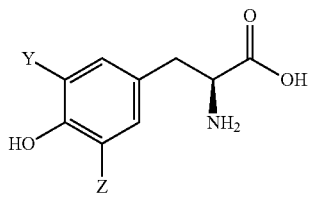

where Y and Z are each independently any element. In some embodiments, Y and/or Z are a halogen. In some embodiments, one of X or Y is a halogen and the other is a hydrogen. In some embodiments, Y and/or Z is one or more of F, Cl, Br, I and At. In some embodiments, one of Y and Z is hydrogen and one of Y and Z is selected from F, Cl, Br, I and At. In a specific embodiment, Y is hydrogen and Z is selected from F, Cl, Br, I and At. In some embodiments, the non-classical amino acid is mono-iodo-tyrosine, a/k/a N-Iodo-L-tyrosine ("YmI"). In some embodiments, the non-classical amino acid is 3,5-dibromotyrosine. In specific embodiments, the tyrosine derivative precedes the sequence CRTSC (SEQ ID NO: 15) or CRQSC (SEQ ID NO: 16).

Alternatively or additionally the sensor, e.g. the chelator molecule (e.g. peptide) includes an element having an atomic number greater 11. In yet another embodiment of the method the solid support, e.g. resin, comprises a chemical element having an atomic number greater than 11. Optionally, the method can also include measuring a sample of the element. Optionally the method can further include calculating the ratio between a metal and/or metalloid element (e.g. selenium) and the element. In various embodiments, the chemical element having an atomic number greater than 11 is useful as an internal quantitative standard for the measurement methods of the present invention (e.g. the element is present at a known stoichiometry). In various embodiments, the chemical element having an atomic number greater than 11 is useful as a barcoding system for identification of the chelator in a mixture or unordered array.

In various embodiments, the element may be one or more of 12: Magnesium, 13: Aluminum, 14: Silicon, 15: Phosphorus, 16: Sulfur, 17: Chlorine, 18: Argon, 19: Potassium, 20: Calcium, 21: Scandium, 22: Titanium, 23: Vanadium, 25: Manganese, 26: Iron, 27: Cobalt, 28: Nickel, 29: Copper, 30: Zinc, 31: Gallium, 32: Germanium, 33: Arsenic, 35: Bromine, 36: Krypton, 37: Rubidium, 38: Strontium, 39: Yttrium, 40: Zirconium, 41: Niobium, 42: Molybdenum, 43: Technetium, 44: Ruthenium, 45: Rhodium, 46: Palladium, 47: Silver, 48: Cadmium, 49: Indium, 50: Tin, 51: Antimony, 52: Tellurium, 53: Iodine, 54: Xenon, 55: Cesium, 56: Barium, 57: Lanthanum, 58: Cerium, 59: Praseodymium, 60: Neodymium, 61: Promethium, 62: Samarium, 63: Europium, 64: Gadolinium, 65: Terbium, 66: Dysprosium, 67: Holmium, 68: Erbium, 69: Thulium, 70: Ytterbium, 71: Lutetium, 72: Hafnium, 73: Tantalum, 74: Tungsten, 75: Rhenium, 76: Osmium, 77: Iridium, 78: Platinum, 79: Gold, 80: Mercury, 81: Thallium, 82: Lead, 83: Bismuth, 84: Polonium, 85: Astatine, 86: Radon, 87: Francium, 88: Radium, 89: Actinium, 90: Thorium, 91: Protactinium, 92: Uranium, 93: Neptunium, 94: Plutonium, 95: Americium, 96: Curium, 97: Berkelium, 98: Californium, 99: Einsteinium, 100: Fermium, 101: Mendelevium, 102: Nobelium, 103: Lawrencium, 104: Rutherfordium, 105: Dubnium, 106: Seaborgium, 107: Bohrium, 108: Hassium, 109: Meitnerium, 110: Darmstadtium, 111: Roentgenium, 112: Copernicium, 113: Ununtrium, 114: Flerovium, 115: Ununpentium, 116: Livermorium, 117: Ununseptium, and 118: Ununoctium.

In some embodiments, the element is Se, Br, I, Cl, S, or P.

For example, in some embodiments, the present invention is used to determine a ratio of selenium to a second element, or third element, or fourth element or fifth element. For example, in some embodiments, the present invention is used to determine a ratio of selenium to bromine.

In some embodiments, the sensor and/or array of sensors comprises a peptide and has a structure selected from F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBr-CRTSC-RESIN (SEQ ID NO: 10-RESIN), YBrCRQSC-RESIN (SEQ ID NO: 11-RESIN)), F4ICDICPNHC-RESIN (SEQ ID NO: 6-RESIN), F4ICQRCERWC-RESIN (SEQ ID NO: 7-RESIN), F4ICHTCFQTC-RESIN (SEQ ID NO: 8-RESIN), and YmICR(T/Q)SC-RESIN (SEQ ID NO: 12-RESIN) (e.g. YmICRTSC (SEQ ID NO: 13)-RESIN, YmICRQSC (SEQ ID NO: 14)-RESIN) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-F4ICDICPNHC (RESIN-SEQ ID NO: 6), RESIN-F4ICQRCERWC (SEQ ID NO: 7), RESIN-F4ICHTCFQTC (RESIN-SEQ ID NO: 8), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)), and RESIN-YmICR(T/Q)SC (RESIN-SEQ ID NO: 12) (e.g. RESIN YmICRTSC (RESIN-SEQ ID NO: 13), RESIN-YmICRQSC (RESIN-SEQ ID NO: 14)).

In some embodiments, the sensor and/or array of sensors comprises a peptide and has a structure selected from F4ICDICPNHCF4Br-PEG4-Polystyrene (SEQ ID NO: 1-PEG4-Polystyrene), F4ICQRCERWCF4Br-PEG4-Polystyrene (SEQ ID NO: 2-PEG4-Polystyrene), F4ICFHCFSECF4Br-PEG4-Polystyrene (SEQ ID NO: 3-PEG4-Polystyrene), F4ICAGCFTGCF4Br-PEG4-Polystyrene (SEQ ID NO: 4-PEG4-Polystyrene), F4ICQLCNVLCF4Br-PEG4-Polystyrene (SEQ ID NO: 5-PEG4-Polystyrene), YBrCR(T/Q)SC-PEG4-Polystyrene (SEQ ID NO: 9-PEG4-Polystyrene) (e.g. YBrCRTSC-PEG4-Polystyrene (SEQ ID NO: 10-PEG4-Polystyrene), YBrCRQSC-PEG4-Polystyrene (SEQ ID NO: 11-PEG4-Polystyrene)) and YmICR(T/Q)SC-PEG4-Polystyrene (SEQ ID NO: 12-PEG4-Polystyrene) (e.g. YmICRTSC-PEG4-Polystyrene (SEQ ID NO: 13-PEG4-Polystyrene), YmICRQSC-PEG4-Polystyrene (SEQ ID NO: 14-PEG4-Polystyrene) or Polystyrene-PEG4-F4ICDICPNHCF4Br (Polystyrene-PEG4-SEQ ID NO: 1), Polystyrene-PEG4-F4ICQRCERWCF4Br (Polystyrene-PEG4-SEQ ID NO: 2), Polystyrene-PEG4-F4ICFHCFSECF4Br (Polystyrene-PEG4-SEQ ID NO: 3), Polystyrene-PEG4-F4ICAGCFTGCF4Br (Polystyrene-PEG4-SEQ ID NO: 4), Polystyrene-PEG4-F4ICQLCNVLCF4Br (Polystyrene-PEG4-SEQ ID NO: 5), Polystyrene-PEG4-YBrCR(T/Q)SC (Polystyrene-PEG4-SEQ ID NO: 9) (e.g. Polystyrene-PEG4-YBrCRTSC (Polystyrene-PEG4-SEQ ID NO: 10), Polystyrene-PEG4-YBrCRQSC (Polystyrene-PEG4-SEQ ID NO: 11)) and Polystyrene-PEG4-YmICR(T/Q)SC (Polystyrene-PEG4-SEQ ID NO: 12) (e.g. Polystyrene-PEG4-YmICRTSC (Polystyrene-PEG4-SEQ ID NO: 13), Polystyrene-PEG4-YmICRQSC (Polystyrene-PEG4-SEQ ID NO: 14)).

In some embodiments the solution comprises selenate and the sensor and/or array of sensors comprises a peptide and has a structure selected from F4ICDICPNHCF4Br-RESIN (SEQ ID NO:1-RESIN), F4ICQRCERWCF4Br-RESIN (SEQ ID NO:2-RESIN), F4ICFHCFSECF4Br-RESIN (SEQ ID NO: 3-RESIN). In some embodiments the solution comprises selenate and the resin comprises a peptide and has a structure selected from F4ICDICPNHCF4Br-PEG4-Polystyrene (SEQ ID NO:1-PEG4-Polystyrene), F4ICQRCERWCF4Br-PEG4-Polystyrene (SEQ ID NO:2-PEG4-Polystyrene), F4ICFHCFSECF4Br-PEG4-Polystyrene (SEQ ID NO: 3-PEG4-Polystyrene).

In some embodiments the solution comprises selenite and the sensor and/or array of sensors comprises a peptide and has a structure selected from F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)). In some embodiments the solution comprises selenite and the sensor and/or array of sensors comprises a peptide and has a structure selected from F4ICAGCFTGCF4Br-PEG4-Polystyrene (SEQ ID NO: 4-PEG4-Polystyrene), F4ICQLCNVLCF4Br-PEG4-Polystyrene (SEQ ID NO: 5-PEG4-Polystyrene), YBrCR(T/Q)SC-PEG4-Polystyrene (SEQ ID NO: 9-PEG4-Polystyrene) (e.g. YBrCRTSC-PEG4-Polystyrene (SEQ ID NO: 10-Polystyrene-PEG4), YBrCRQSC-PEG4-Polystyrene (SEQ ID NO: 11-PEG4-Polystyrene)) and YmICR(T/Q)SC-PEG4-Polystyrene (SEQ ID NO: 12-PEG4-Polystyrene) (e.g. YmICRTSC-PEG4-Polystyrene (SEQ ID NO: 13-PEG4-Polystyrene), YmICRQSC-PEG4-Polystyrene (SEQ ID NO: 14-PEG4-Polystyrene)).

In a specific embodiment, the invention provides a composition comprising a sensor and/or array of sensors, which is comprises a peptide. In a specific embodiment, the invention provides a composition comprising a sensor and/or array of sensors, which comprises a peptide, the peptide comprising one or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)) and YmICR(T/Q)SC (SEQ ID NO: 12) (e.g. YmICRTSC (SEQ ID NO: 13), YmICRQSC (SEQ ID NO: 14)), or variants thereof. In some embodiments, the composition comprises two or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)), or variants thereof. In some embodiments, the composition comprises three or more of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. In some embodiments, the composition comprises four of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. In some embodiments, the composition comprises five of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. In some embodiments, the composition comprises six of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)) or variants thereof. Such compositions may find use in detection of one or both of selenite and selenate. Such peptides may bind an analyte at differing affinities as described elsewhere herein.

In a specific embodiment, the invention provides a sensor and/or array of sensors comprising a resin, which is associated with a peptide for the detection of selenate, the peptide having a sequence selected from F4ICDICPNHCF4Br (SEQ ID NO: 1), F4ICQRCERWCF4Br (SEQ ID NO: 2), F4ICFHCFSECF4Br (SEQ ID NO: 3), or variants thereof.

In a specific embodiment, the invention provides a sensor and/or array of sensors comprising a resin, which is associated with a peptide for the detection of selenite, the peptide having a sequence selected from F4ICAGCFTGCF4Br (SEQ ID NO: 4), F4ICQLCNVLCF4Br (SEQ ID NO: 5), YBrCR(T/Q)SC (SEQ ID NO: 9) (e.g. YBrCRTSC (SEQ ID NO: 10), YBrCRQSC (SEQ ID NO: 11)), and YmICR(T/Q)SC (SEQ ID NO: 12) (e.g. YmICRTSC (SEQ ID NO: 13), YmICRQSC (SEQ ID NO: 14)), or variants thereof.

As described above, the peptides of the sensor and/or array of sensors may be mutated.

The present sensor and/or array of sensors may comprise one or more of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmICRQSC (RESIN-SEQ ID NO: 14)). The present sensor and/or array of sensors may comprise one of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmICRQSC (RESIN-SEQ ID NO: 14)). The present sensor and/or array of sensors may comprise two of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmICRQSC (RESIN-SEQ ID NO: 14)). The present sensor and/or array of sensors may comprise three of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmICRQSC (RESIN-SEQ ID NO: 14)). The present sensor and/or array of sensors may comprise four of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN- YmICRTSC (RESIN-SEQ ID NO: 13), RESIN-YmI-CRQSC (RESIN-SEQ ID NO: 14)). The present sensor and/or array of sensors may comprise five of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (RESIN-SEQ ID NO: 10), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmI-CRQSC (RESIN-SEQ ID NO: 14)). The present sensor and/or array of sensors may comprise six of F4ICDICPNHCF4Br-RESIN (SEQ ID NO: 1-RESIN), F4ICQRCERWCF4Br-RESIN (SEQ ID NO: 2-RESIN), F4ICFHCFSECF4Br-RESIN (SEQ ID NO: 3-RESIN), F4ICAGCFTGCF4Br-RESIN (SEQ ID NO: 4-RESIN), F4ICQLCNVLCF4Br-RESIN (SEQ ID NO: 5-RESIN), YBrCR(T/Q)SC-RESIN (SEQ ID NO: 9-RESIN) (e.g. YBrCRTSC-RESIN (SEQ ID NO: 10-RESIN), YBrCRQSC-RESIN (SEQ ID NO: 11-RESIN)) and YmICR(T/Q)SC-RESIN (SEQ ID NO: 12-RESIN) (e.g. YmICRTSC-RESIN (SEQ ID NO: 13-RESIN), YmICRQSC-RESIN (SEQ ID NO: 14-RESIN)) or RESIN-F4ICDICPNHCF4Br (RESIN-SEQ ID NO: 1), RESIN-F4ICQRCERWCF4Br (RESIN-SEQ ID NO: 2), RESIN-F4ICFHCFSECF4Br (RESIN-SEQ ID NO: 3), RESIN-F4ICAGCFTGCF4Br (RESIN-SEQ ID NO: 4), RESIN-F4ICQLCNVLCF4Br (RESIN-SEQ ID NO: 5), RESIN-YBrCR(T/Q)SC (RESIN-SEQ ID NO: 9) (e.g. RESIN-YBrCRTSC (SEQ ID NO: 10-RESIN), RESIN-YBrCRQSC (RESIN-SEQ ID NO: 11)) and RESIN-YmICR(T/Q)SC (RESIN-SEQ ID NO: 12) (e.g. RESIN-YmICRTSC (RESIN-SEQ ID NO: 13), RESIN-YmI-CRQSC (RESIN-SEQ ID NO: 14)).

In some embodiments the sensor and/or array of sensors comprises a structure F4ICDICPNHCF4Br-RESIN (SEQ ID NO: 1-RESIN), which binds selenate anion ($SeO_4^{2-}$). In some embodiments the sensor and/or array of sensors comprises a structure F4ICQRCERWCF4Br-RESIN (SEQ ID NO: 2-RESIN), which binds selenate anion ($SeO_4^{2-}$). In some embodiments the sensor and/or array of sensors comprises a structure F4ICFHCFSECF4Br-RESIN (SEQ ID NO: 3-RESIN), which binds selenate anion ($SeO_4^{2-}$).

In some embodiments, the sensor and/or array of sensors comprises a structure F4ICAGCFTGCF4Br-RESIN (SEQ ID NO: 4-RESIN), which binds selenite anion ($SeO_3^{2-}$). In some embodiments, the sensor and/or array of sensors comprises a structure F4ICQLCNVLCF4Br-RESIN (SEQ ID NO: 5-RESIN), which binds selenite anion ($SeO_3^{2-}$). In some embodiments the sensor and/or array of sensors comprises a structure YBrCRTSC-RESIN (SEQ ID NO: 10-RESIN), which binds selenite anion ($SeO_3^{2-}$). In some embodiments, the sensor and/or array of sensors comprises a structure YBrCRQSC-RESIN (SEQ ID NO: 11-RESIN), which binds selenite anion ($SeO_3^{2-}$). In some embodiments, the sensor and/or array of sensors comprises a structure YmICRTSC-RESIN (SEQ ID NO: 13-RESIN), which binds selenite anion ($SeO_3^{2-}$). In some embodiments, the sensor and/or array of sensors comprises a structure YmICRQSC-RESIN (SEQ ID NO: 14-RESIN), which binds selenite anion ($SeO_3^{2-}$).

In some embodiments, the sensor and/or array of sensors is used for measuring both selenate and selenite, e.g. to find a ratio of species, and comprises one of F4ICDICPNHCF4Br-RESIN (SEQ ID NO: 1-RESIN), F4ICQRCERWCF4Br-RESIN (SEQ ID NO: 2-RESIN), and 4ICFHCFSECF4Br-RESIN and one of F4ICAGCFTGCF4Br-RESIN (SEQ ID NO: 4-RESIN), F4ICQLCNVLCF4Br-RESIN (SEQ ID NO: 5-RESIN), YBrCRTSC-RESIN (SEQ ID NO: 10-RESIN), YBrCRQSC-RESIN (SEQ ID NO: 11-RESIN), YmICRTSC-RESIN (SEQ ID NO: 13-RESIN), and YmICRQSC-RESIN (SEQ ID NO: 14-RESIN)).

In some embodiments, the sensor and/or array of sensors comprises any peptide described herein.

Methods of Detecting Metals and/or Metalloids

In some aspects, the present invention relates to method for measuring a metal and/or metalloid element. In various embodiments, the method involves contacting a sample comprising a metal and/or metalloid element with a sensor or array of sensors that is suitable for concentrating a metal and/or metalloid element and measuring the metal and/or metalloid element on the sensor or array of sensors.

In some aspects, the invention provides a method for measuring selenium, inclusive of, for example, selenate or selenite, in a sample, for example a liquid sample. Such method includes, in various embodiments, contacting (e.g., combining) a solution containing selenium and a sensor or array of sensors capable of concentrating the selenium from the sample (e.g. solution). In various embodiments, the method also includes measuring a sample of the selenium that is concentrated on the sensor or array of sensors. The measurement can be, for example, an elemental analysis method as described herein.

In some aspects, the present invention relates to method for selectively measuring a valence or oxidation state of a metal and/or metalloid element. In various embodiments, the method involves contacting a sample comprising a metal and/or metalloid element with a resin that is suitable for concentrating a particular valence or oxidation state of the metal and/or metalloid element and measuring a particular valence or oxidation state of metal and/or metalloid element on the resin.

Illustrative metal elements are as follows: 3: Lithium, 4: Beryllium, 11: Sodium, 12: Magnesium, 13: Aluminum, 19: Potassium, 20: Calcium, 21: Scandium, 22: Titanium, 23: Vanadium, 24: Chromium, 25: Manganese, 26: Iron, 27: Cobalt, 28: Nickel, 29: Copper, 30: Zinc, 31: Gallium, 37: Rubidium, 38: Strontium, 39: Yttrium, 40: Zirconium, 41: Niobium, 42: Molybdenum, 43: Technetium, 44: Ruthenium, 45: Rhodium, 46: Palladium, 47: Silver, 48: Cadmium, 49: Indium, 50: Tin, 55: Cesium, 56: Barium, 57: Lanthanum, 58: Cerium, 59: Praseodymium, 60: Neodymium, 61: Promethium, 62: Samarium, 63: Europium, 64: Gadolinium, 65: Terbium, 66: Dysprosium, 67: Holmium, 68: Erbium, 69: Thulium, 70: Ytterbium, 71: Lutetium, 72: Hafnium, 73: Tantalum, 74: Tungsten, 75: Rhenium, 76: Osmium, 77: Iridium, 78: Platinum, 79: Gold, 80: Mercury, 81: Thallium, 82: Lead, 83: Bismuth, 87: Francium, 88: Radium, 89: Actinium, 90: Thorium, 91: Protactinium, 92: Uranium, 93: Neptunium, 94: Plutonium, 95: Americium, 96: Curium, 97: Berkelium, 98: Californium, 99: Einsteinium, 100: Fermium, 101: Mendelevium, 102: Nobelium, 103: Lawrencium, 104: Rutherfordium, 105: Dubnium, 106: Seaborgium, 107: Bohrium, 108: Hassium, 109: Meitnerium, 110: Darmstadtium, 111: Roentgenium, 112: Copernicium, 113: Ununtrium, 114: Flerovium, 115: Ununpentium, and 116: Livermorium.

Illustrative metalloid elements are as follows: 5: Boron, 14: Silicon, 32: Germanium, 33: Arsenic, 34: Selenium, 51: Antimony, and 52: Tellurium.

Selenium, atomic number 34, is a metalloid element. Selenium can be found in $-2$, $0$, $+4$, and $+6$ oxidation states. All of these oxidation states may be detected, i.e. $-2$, $0$, $+4$, and $+6$, optionally selectively, using the present invention. For instance, in one embodiment, the present invention distinguishes selenate from selenite. For example, the present invention may provide a quantitative or qualitative output of selenate and/or selenite. Alternatively, the present invention may be useful in determining the ratio selenate to selenite. However, in other embodiments, the present invention may be useful in determining total selenium.

Furthermore, in various embodiments, the present invention can detect, optionally selectively, one or more isotopes of selenium, i.e. $^{74}Se$, $^{75}Se$, $^{76}Se$, $^{77}Se$, $^{78}Se$, $^{80}Se$, and $^{82}Se$.

In various embodiments, the present invention involves or allows for the detection of a variety of selenium-based compounds, including without limitation: niobium triselenide, oxyselenide, selenium dioxide, selenium disulfide, selenium hexafluoride, selenium hexasulfide, selenium monochloride, selenium oxybromide, selenium oxydichloride, selenium tetrachloride, selenium tetrafluoride, selenium trioxide, and selenoyl fluoride.

Furthermore, in various embodiments, the present invention allows for the detection of a ratio of a metal and/or metalloid element, inclusive of selenium, to another element as described elsewhere herein.

The present invention finds use, in some embodiments, in environmental detection and protection. For instance, the present invention may be used to assess metal and/or metalloid contamination (e.g. selenium contamination) in soil and/or groundwater (e.g. at current or abandoned industrial sites). In some embodiments, the invention relates to environmental cleanup and remediation, e.g. the treatment of brownfield land. The present invention finds use, in some embodiments, in detection of metal and/or metalloid concentrations (e.g. selenium concentration) in wastewater. The present invention finds use, in some embodiments, in detection of metal and/or metalloid concentrations (e.g. selenium concentration) in wastewater near power plants and industrial sources.

The present invention finds use in monitoring human consumption of metal and/or metalloid elements (e.g. selenium). For instance, the present invention, in various embodiments, relates to analysis of drinking water. For instance, the present invention, in various embodiments, relates to analysis of the portability of water. In other embodiments, the present invention allows for measuring metal and/or metalloid elements (e.g. selenium) in food or soil (e.g. of agricultural spaces).

Further, and relatedly, the present invention, in various embodiments, relates to analysis, e.g. quality monitoring, of one or more of environmental water, ground water, surface water, and wastewater.

In various embodiments, the present invention relates to detection of elements before and after environment treatments. For example, in some embodiments, the present invention provides a means to compare a sample's metal and/or metalloid (e.g. selenium) elemental composition before and after treatments. For example, such methods can evaluate the success or failure of methods for removing metal and/or metalloid (e.g. selenium) element from a sample, including ion exchange. In the case of selenium, the present methods may be used to evaluate the success or failure of one or more of activated alumina, coagulation/filtration, lime softening, reverse osmosis, and electrodialysis to remove selenium from a sample.

Selenium has been characterized as an environmental source of pollution, e.g. from waste materials from certain mining, agricultural, petrochemical, and industrial manufacturing operations. For example, in Belews Lake, N.C., 19 species of fish were eliminated from the lake due to 150-200 μg Se/L wastewater discharged from 1974 to 1986 from a Duke Energy coal-fired power plant. Also, at the Kesterson National Wildlife Refuge in California, thousands of fish and waterbirds were poisoned by selenium in agricultural irrigation drainage.

U.S. EPA has set a maximum contaminant level goals (MCLG) for selenium of 0.05 mg/L or 50 ppb. In various embodiments, the present invention may be used to confirm compliance with such standard.

Illustrative Analytes

The methods, compositions and apparatus described herein can be compatible with complex fluid matrix carriers of an analyte such a metal- and/or metalloid-containing analyte (e.g., wherein the analyte is dissolved, suspended or otherwise combined with). For instance, the analyte can contain selenium. For example solutions utilized can be from agricultural run-off. Fertilizers can contain trace amounts of selenium and such run-off can include selenate and selenite ions. Other example include run-off, e.g. wastewater, from mining operations and power plants. For example, when coal-bearing strata are exposed to air and water during the mining process, and when coal is washed prior to transportation and distribution. Such runoff as from agriculture, coal and petroleum operations can include many other ions and other materials.

In other examples, the solution utilized can include a biological fluid (e.g., including biological stimulant). The biological fluids can be, or be formulated to simulate, the fluids extracted or produced from plants, animals, humans, yeast and/or bacteria. Such fluids can be naturally sourced or are simulated (e.g., including using naturally source ingredients and/or unnaturally sourced ingredients). For example, such fluids can include blood plasma, synovial fluid, urine, gastric fluid (e.g., fasted-state gastric fluid or fed-state gastric fluid), intestinal fluid, (e.g., fasted-state intestinal fluid, fed-state intestinal fluid) colonic fluid, fasted-state colonic fluid, fed-state colonic fluid, saliva, lung fluid, fluid from exhaled breath, vaginal fluid, semen, tears, sweat, cerebrospinal fluids, cerumen, endolymph, perilymph, feces, milk, bronchial fluids, amniotic fluid, aqueous humor, vitreous humor, bile, chyle, chyme, exudate, intracellular fluid, interstitial fluid, lymphatic fluid, transcellular fluid, plant exudates, female ejaculate, gastric acid, gastric juice, mucus, pericardial fluid, pleural fluid, pus, rheum, sebum, sputum, vomit, and mixtures of these. Such fluids can be derived from an animal, e.g. human, believed to have been exposed a metal and/or metalloid element, such as selenium. Such fluids can include many compounds and can be undefined or uncharacterized.

Detection Methods/Measurements/Elemental Analysis

In various embodiments, the present methods, apparatus, sensors and/or array of sensors, and compositions use, or can be used with, a variety of detection methods, including, without limitation x-ray fluorescence, atomic absorption spectroscopy, atomic emission spectroscopy, mass spectrometry, and laser induced breakdown spectroscopy.

X-ray fluorescence spectroscopy can be a useful method for the implementation of some of the embodiments herein described. X-ray fluorescence spectrometry is a spectroscopic technique that can be used to determine one or more chemical elements (e.g., heavy metals) that are present in a sample, such as can be present in an analyte, a molecule, a polymer, a mineral, an organelle, a tissue, a biological fluid, an organ, an inorganic materials (e.g., clays, sands, silt, rocks and low organic containing soils), organic material (e.g., biomass such as plants, animals, insects, yeast, bacterial and/or high organic containing soil) or other substrates. The method can be used to qualitatively identify and also quantify the elements present and relies on the underlying physical principle that when an atom of a particular element is irradiated with x-ray radiation, the atom ejects a core electron such as a K, L or M shell electron. The resulting atom is in an excited state, such as a $1S^1$ excited state, and it can return to the ground state by replacing the ejected electron with an electron from a higher energy orbital. This transition is accompanied by the emission of a photon, in the process known as x-ray fluorescence, and the photon energy is equal to the difference in the energies of the two orbitals. Each element has a characteristic set of orbital energies and therefore, a characteristic x-ray fluorescence spectrum. For example, each element will have a characteristic x-ray energy signal corresponding to the energies of the K, L and M electron shells of each element.

X-ray fluorescence can be generated by excitation of atoms by a beam of electrons, particles and/or x-rays. Samples, such as described herein, subjected to such excitation can produce x-ray fluorescence due to the elements in the samples and one or more of the elements can be monitored. For example, Particle-Induced X-ray Emission (PIXE) and X-ray Fluorescence (XRF) can be used. In some embodiments, XRF is used in the embodiments described herein. In some embodiments, μ-XRF is used.

In some embodiments, the x-ray fluorescence is energy dispersive x-ray fluorescence. Optionally, the x-ray fluorescence utilizes polychromatic x-rays for exciting the sample. In some embodiments the analysis method is an x-ray fluorescence that utilizes a micro-focus x-ray tube. Optionally, the x-ray fluorescence utilizes a focusing optic.

An x-ray fluorescence spectrometer is an apparatus capable of irradiating a sample with an x-ray beam, and detecting the x-ray fluorescence from the sample. The irradiation can be produced by various sources, such as synchrotron radiation, a radioactive source or an x-ray tube. Synchrotron radiation can produce a monochromatic x-ray beam with a very high intensity. The bending, beam focusing and particle acceleration needed to produce synchrotron radiation requires a larger scale facility with concomitant expenses. Regarding radioactive sources, x-rays from radioactive primary sources such as $^{55}$Fe, $^{109}$Cd and $^{241}$Am can be made to strike a secondary exciter target, e.g., tin, and the characteristic x-rays from the exciter target are aimed at the unknown sample. Radioactive sources produce beams with the characteristic lines of the secondary exciter target and have very low energies elsewhere. X-ray tubes produce polychromatic x-rays including a very broad "Bremsstrahlung" radiation band and characteristic emission peaks. X-ray tubes offer analytical flexibility in the beam energies, for example by changing the applied voltage and target material of the x-ray tube. Filters can also be added to narrow or exclude certain energies (e.g., high pass, low pass or band pass filters). Focusing optics can be used such as collimators and/or concentrators (e.g., mono capillary and polycapillary) to produce spot sizes smaller than a millimeter in diameter. The fluorescence can be detected in at least two ways, using wavelength dispersive or energy dispersive methods. Wavelength dispersive detectors work by reflecting sample radiation onto an analyzing crystal and measurement of the angle of reflection followed by calculation of the wavelength using Bragg's Law. Energy dispersive detectors work by generating a signal that is proportional to the absorbed energy of a single photon. For example, solid state detectors include gas filled detectors and semiconductor detectors (e.g., PIN diode, silicon drift detectors, Si(Li), SI PIN detector, silicon drift detector, SiLi detector, CdTe, Diamond, Germanium detectors, ion chamber detectors, and the like). The angle of excitation and detector can be between about 0 and about 180 deg. For example angles can be between about 5 DEG and about 95 DEG such as for XRF and μ-XRF. In some instances very low angles, such as below 0.5 DEG can be used, such as when using Total Reflection X-ray Fluorescence (TXRF) and grazing emission x-ray fluorescence. The above methods and components can be utilized to detect x-ray fluorescence in the samples described herein, including using modified commercial equipment. In some embodiments, the methods use at least one x-ray tube (e.g., having Cu, Mo, Cr, W or Rh targets), polycapillary focusing optics and one or more solid state detectors (e.g., one or two detectors). For example, polychromatic x-rays generated from an x-ray tube can be focused to less than 5 mm diameter (e.g., less that about 4 mm diameter, less than about 3 mm diameter, less than about 2 mm diameter, less than about 1 mm diameter, less than about 750 μm diameter, less than about 500 μm diameter, less than about 100 μm diameter or even less than about 50 μm diameter) spot size and detected using a silicon drift detector.

In various embodiments, the present invention provides for alterations of the x-ray fluorescence spectrometer to allow for efficient detection of desired analytes. For instance, the x-ray fluorescence spectrometer may be altered to provide excitation at photon energies that are best suited for the desired analytes. For example, the choice of x-ray tube material, excitation filters or monochrometer may be altered to best suit the desired analytes.

X-ray fluorescence is inefficient relative to the excitation energy of the exciting beam (e.g., x-ray excitation beam). For light elements, for example with atomic numbers below about 10, the fluorescence yields are practically zero for all lines. Above about atomic number 10 the efficiency for the K line increases from zero to only about 0.1 at atomic number 20 after which it starts rising more significantly. The efficiency for the L line is zero until about atomic number 30 and is only about 0.1 for atomic number 60. In some instances, it is advantageous to maintain a vacuum between the sample and detector path to mitigate the attenuation due to components in air especially for lighter elements (e.g., between atomic number 10 and about 20). Optionally, the path between the sample and detector can be kept under an atmosphere of a light element such as helium.

In energy dispersive XRF, the characteristic radiation of a particular line can be described approximately as a Gaussian function (e.g., a detector response function). The spectral background results from a variety of processes such as incoherent scattered primary radiation and therefore depends on the shape of the excitation spectrum and on the sample composition. In embodiments, the characteristic signal of an analyte (e.g., element) of interest such as a heavy metal produces a signal in at least one area of the spectrum such as a peak with a signal to noise ratio of at least 3. One method to obtain the net data area under a line of interest consists of interpolating the background under the peak and summing the background-corrected channel contents in a window over the peak. This approach can be limited by the curvature of the background and by the presence of other peaks and other peak deconvolution methods can be used to better resolve the spectrum. A resolved peak is understood that the peak energy (e.g., position) and counts under a peak (e.g., integrated area) can be determined and associated to a particular element.

A widely used method for peak resolution (e.g., deconvolution) is non-linear least squares fitting of the spectral data with an analytical function. This algebraic function, including all important parameters (e.g., net areas of the fluorescent lines, their energy and resolution) is used as a model for the measured spectrum. It consists of the contribution from all peaks (e.g., modified Gaussian peaks with corrections for low-energy tailing and escape peaks) within a certain region of interest and the background (e.g., described by, for example, linear or exponential polynomials). The optimum values of the parameters are those for which the difference between the model and the measured spectrum is minimal. Some of the parameters are nonlinear, and a minimization procedure is selected such as the Marquardt algorithm.

Another method for peak resolution applies a top-hat filter to suppress low frequency components in the spectrum. This method reduces or even eliminates the background but also can distort the spectrum. In the method, the top hat filter is applied to a well-defined reference spectrum (e.g., of know concentrations of elements) as well as the experimental spectrum with unknowns and the two are compared. The comparison can be, for example, by applying a multiple linear least-squares fitting to the filtered spectra resulting in the net peak areas of interest.

Other deconvolution protocols can be used to resolve the peaks of interest. Backgrounds can vary between about zero counts per second (cps) and about 10,000 cps dependent at least in part on the deconvolution protocol used. It is be understood by those skilled in the art what protocol can be utilized.

Further methods involving x-ray fluorescence are described in U.S. Pat. Nos. 7,858,385; 7,519,145; 7,929,662, and 9,063,066 and U.S. Patent Publication No. 2008-0220441, the entire contents of which are incorporated herein.

In addition to x-ray fluorescence, other elemental analysis methods and their corresponding instruments that are capable of measuring a metal and/or metalloid may also be used with the present invention. These methods include atomic absorption spectroscopy, where the elemental analysis is performed by atomizing the sample and measuring the transmittance of light of various wavelengths through the atomized sample; atomic emission spectroscopy, where the sample is excited, often by burning, and the wavelength and intensity of the emitted light is measured and correlated to the elemental composition of the sample; mass spectrometry; and laser induced breakdown spectroscopy, which is a particular type of atomic emission spectroscopy where the excitation is provided by a laser.

Quantitative Detection

In some embodiments the methods, apparatus and compositions described herein can be utilized to analyze an element, e.g. a metal and/or metalloid element, e.g. selenium present in a sample at various concentrations across a wide dynamic range. In various embodiments, the differing affinities of the various sensors and/or arrays of sensors allow for this detection over a measurable dynamic range. In various embodiments, the measurement can be made in real time, e.g. at the point of sampling.

In various embodiments, the measurement is made on sensors that are still in contact with the sample to be analyzed. In various embodiments, the measurement is made on sensors that are not in contact with the sample to be analyzed, e.g. have been removed from the sample.

In some embodiments the methods, apparatus and compositions described herein can be utilized to analyze an element, e.g. a metal and/or metalloid element, e.g. selenium present in a sample at concentrations above about 50 parts per billion, or above 500 parts per billion, or above one part per million.

For instance, in some embodiments the methods, apparatus and compositions described herein can be utilized to analyze an element, e.g. a metal and/or metalloid element, e.g. selenium, present in a sample at concentrations above about 50 ppb, or above about 75 ppb, or above about 100 ppb, or above about 150 ppb, or above about 200 ppb, or above about 250 ppb, or above about 300 ppb, or above about 350 ppb, or above about 400 ppb, or above about 450 ppb, or above about 500 ppb, or above about 550 ppb, or above about 600 ppb, or above about 650 ppb, or above about 700 ppb, or above about 750 ppb, or above about 800 ppb, or above about 850 ppb, or above about 900 ppb, or above about 950 ppb, or above 1 ppm, or above 5 ppm, or above 10 ppm, or above 100 ppm. In some embodiments the methods, apparatus and compositions described herein can be utilized to analyze an element, e.g. a metal and/or metalloid element, e.g. selenium, present in a sample at concentrations at or below about 10 ppb, or at or below about 25 ppb, or at or below about 50 ppb, or at or below about 75 ppb, or at or below about 100 ppb, or at or below about 150 ppb.

Apparatus

In various embodiments, the present invention provides an apparatus which finds use in, for instance, measuring metals and/or metalloids, such as selenium, that have been absorbed on a solid support, e.g. resin. In various embodiments, the present invention provides an apparatus comprising the resins described herein.

Figure 2:
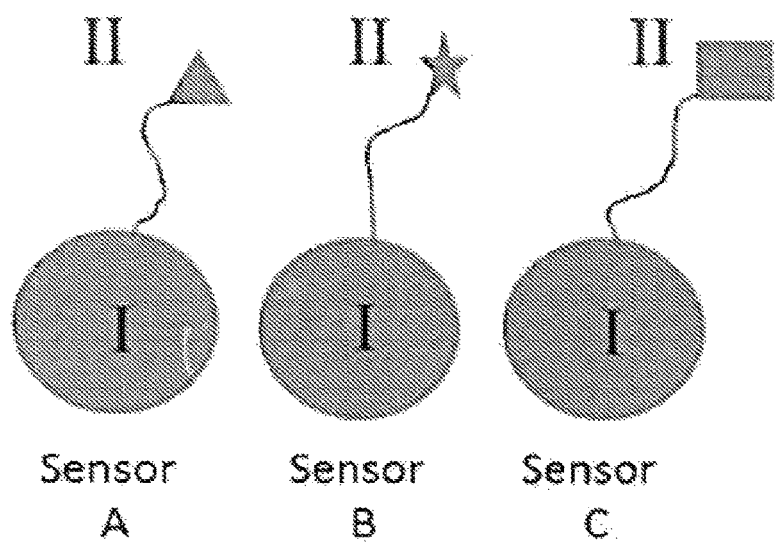
FIG. 2 shows a schematic of an illustrative sensor and/or array of sensors described herein (without limitation, FIG. 2, in some embodiments is element 114 of FIG. 1).
Figure 3:
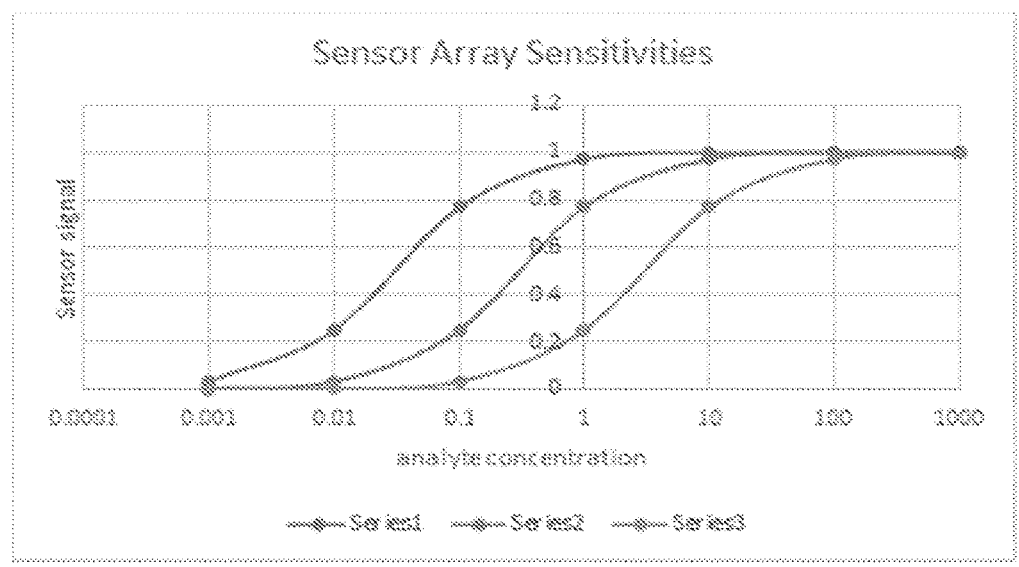
as shown in FIG. 3)

By way of illustration, FIG. 1 shows an embodiment of an apparatus for measuring various metal and/or metalloid elements, such as selenium that has been absorbed on solid support, e.g. resin. The apparatus 100 includes an x-ray excitation source 110 an x-ray detector 112, and a sensor and/or array of sensors 114 (e.g., without limitation as shown in FIG. 2), which is described in more specific detail elsewhere herein. The sensor and/or array of sensors can contain a solid support, e.g. resin, which can be in the form of a bead which chelator molecules 116 attached thereupon. The chelator molecules can bind a species such as a metal- and/or metalloid-containing species 118. The excitation source is configured to irradiate the solid support with x-rays 120. The detector is configured to detect fluorescing x-rays 122 emitted from the solid support, e.g. resin.

FIG. 1 depicts a single x-ray source and single detector. Use of multiple detectors can increase the detection limit. For example, using two detectors can double the sensitivity, lowering the detection limit by about thirty percent or doubling the measurement speed (e.g., from 60 seconds per measurement to 30 seconds per measurement). Alternatively, a semiconductor with a larger active surface can also have the same effect.

This invention is further illustrated by the following non-limiting example.

EXAMPLES

Example 1: Detection of Selenium

X-ray fluorescence measurements were obtained with an x-ray fluorescence spectrometer equipped with a microfocus rhodium x-ray tube equipped with a polycapillary focusing optic as the x-ray excitation source, and an energy dispersive silicon drift detector as the x-ray detector, and resins disposed to be excited by the x-ray tube and disposed such that emission from the resin and any selenium bound to the resin were measured by the x-ray detector, as shown in FIG. 1. Measurements were obtained for selenium and bromine.

The following were resins studied (as noted in FIG. 4 and FIG. 5, on the X-axes):

Sequence 1. F4ICDICPNHCF4Br-PEG4-Polystyrene (SEQ ID NO: 1-PEG4-Polystyrene),

Sequence 2. F4ICQRCERWCF4Br-PEG4-Polystyrene (SEQ ID NO: 2-PEG4-Polystyrene),

Sequence 3. F4ICFHCFSECF4Br-PEG4-Polystyrene (SEQ ID NO: 3-PEG4-Polystyrene),

Sequence 4. F4ICAGCFTGCF4Br-PEG4-Polystyrene (SEQ ID NO: 4-PEG4-Polystyrene),

Sequence 5. F4ICQLCNVLCF4Br-PEG4-Polystyrene (SEQ ID NO: 5-PEG4-Polystyrene), and Sequence 6. YBrCR(T/Q)SC-Polystyrene (SEQ ID NO: 9-Polystyrene).

The following solutions were prepared. A "Selenite Solution" was prepared of water having a concentration of selenite of 50 parts per billion. A "Selenate Solution" was prepared of water having a concentration of selenate of 50 parts per billion. A "Wash Solution" was prepared of water having a concentration of sodium chloride of 2 molar.

Figure 4:
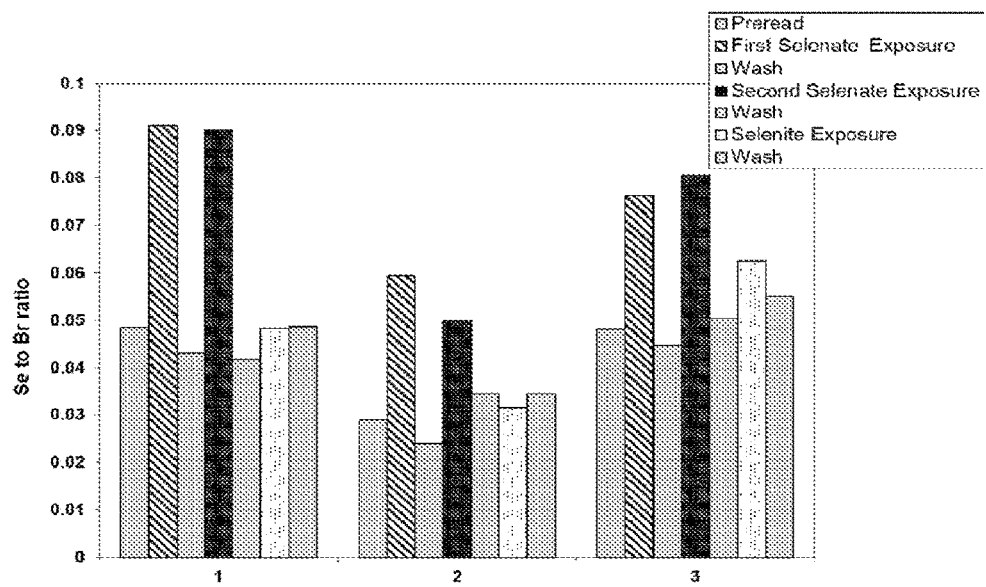
FIG. 4 is a chart showing Se/Br counts for selenate selectivity resins. There are three sets of histograms grouped by bead number and for each set, the histograms are (left to right): preread, first selenate exposure, wash, 2nd selenate exposure, 2nd wash, selenite exposure, and wash.

As shown in FIG. 4, resins 1-3 were measured by x-ray fluorescence to establish a baseline selenium signal, which was standardized to the bromine signal from the resin. Resins 1-3 were then exposed to the Selenate Solution for 12 hours, then measured by x-ray fluorescence, at which time the resins showed elevated selenium signals relative to their baseline selenium signal. Resins 1-3 were then exposed to the Wash Solution for 12 hours, then measured by x-ray fluorescence, at which time they showed selenium signals equal to or less than their baseline signals. Resins 1-3 were then exposed to the Selenate Solution for 12 hours, then measured by x-ray fluorescence, at which time the resins showed elevated selenium signals relative to their baseline selenium signal. Resins 1-3 were then exposed to the Wash Solution for 12 hours, then measured by x-ray fluorescence, at which time they showed selenium signals equal to or less than their baseline signals. Resins 1-3 were then exposed to the Selenite Solution for 12 hours, then measured by x-ray fluorescence, at which time the resins showed selenium signals equal to or less than their baseline signals. Resins 1-3 were then exposed to the Wash Solution for 12 hours, then measured by x-ray fluorescence, at which time they showed selenium signals approximately equal to or less than their baseline signals.

Figure 5:
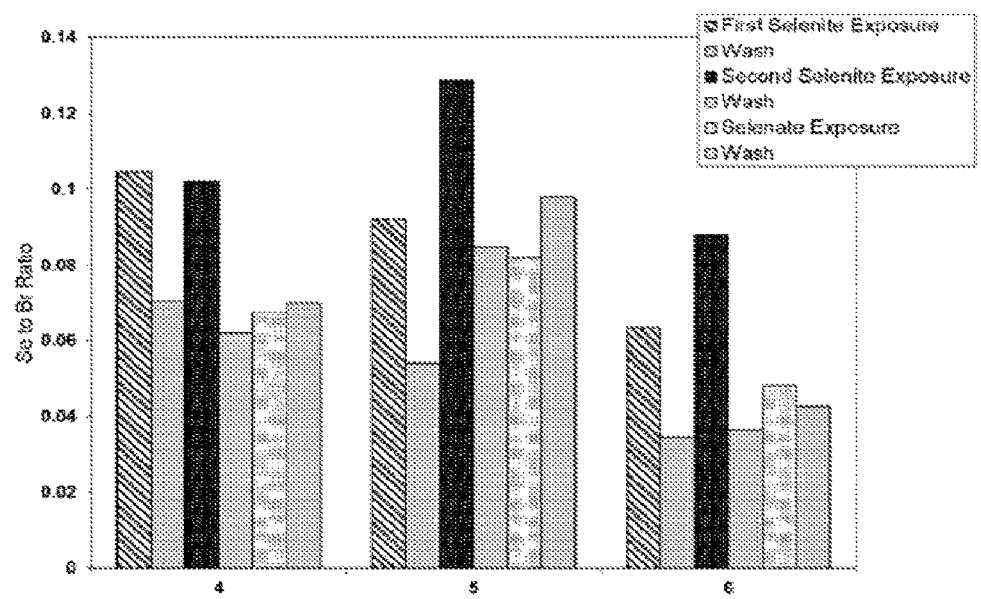
FIG. 5 is a chart showing Se/Br counts for selenite selective resins. There are three sets of histograms grouped by bead number and for each set, the histograms are (left to right): first selenite exposure, wash, second selenite exposure, wash, selenate exposure, wash.

As shown in FIG. 5, Resins 4-6 were measured by x-ray fluorescence to establish a baseline selenium signal, which was standardized to the bromine signal from the resin. Resins 4-6 were then exposed to the Selenite Solution for 12 hours, then measured by x-ray fluorescence, at which time they showed elevated selenium signals relative to their baseline selenium signal. Resins 4-6 were then exposed to the Wash Solution for 12 hours, then measured by x-ray fluorescence, at which time they showed selenium signals equal to or less than their baseline signals. Resins 4-6 were then exposed to the Selenite Solution for 12 hours, then measured by x-ray fluorescence then measured by x-ray fluorescence, at which time they showed elevated selenium signals relative to their baseline selenium signal. Resins 4-6 were then exposed to the Wash Solution for 12 hours, then measured by x-ray fluorescence, at which time they showed selenium signals equal to or less than their baseline signals. Resins 4-6 were then exposed to the Selenate Solution for 12 hours, then measured by x-ray fluorescence, then measured by x-ray fluorescence, at which time the resins showed elevated selenium signals relative to their baseline selenium signal. Resins 4-6 were then exposed to the Wash Solution for 12 hours, then measured by x-ray fluorescence, at which time they showed selenium signals approximately equal to or less than their baseline signals.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

As used herein, all headings are simply for organization and are not intended to limit the disclosure in any manner. The content of any individual section may be equally applicable to all sections.

What is claimed is:

1. A sensor or array of sensors comprising a chelator molecule, wherein the chelator molecule comprises a peptide, the peptide having a general formula of:

$F_1CZ_1Z_2CZ_3Z_4Z_5CF_2$, wherein:

$F_1$ and $F_2$ are each independently a phenylalanine derivative of the structure:

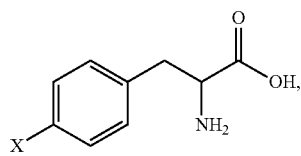

wherein X is a halogen;
C is a cysteine amino acid; and $Z_1$, $Z_2$, $Z_3$, $Z_4$, and $Z_5$ are each independently an amino acid.

2. The sensor or array of sensors of claim 1, wherein $F_1$ is 4-iodophenylalanine (F4I).

3. The sensor or array of sensors of claim 1, wherein $F_2$ is 4-bromophenylalanine (F4Br).

4. The sensor or array of sensors of claim 1, wherein the peptide comprises one or more amino acid sequences of F4ICDICPNHCF4Br (SEQ ID NO: 1), F4ICQRCERWCF4Br (SEQ ID NO: 2), F4ICFHCFSECF4Br (SEQ ID NO: 3), F4ICAGCFTGCF4Br (SEQ ID NO: 4), and F4ICQLCNVLCF4Br (SEQ ID NO: 5), wherein F4I is 4-iodophenylalanine and F4Br is 4-bromophenylalanine.

5. The sensor or array of sensors of claim 1, wherein $Z_1$, $Z_2$, $Z_3$, $Z_4$, and $Z_5$ are each independently an amino acid selected from D, I, P, N, H, Q, R, E, W, S, A, G, F, T, L, V, or modifications thereof.

* * * * *

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 1

Phe Cys Asp Ile Cys Pro Asn His Cys Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 2

Phe Cys Gln Arg Cys Glu Arg Trp Cys Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 3

Phe Cys Phe His Cys Phe Ser Glu Cys Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
```

```
<220> FEATURE:
<221> NAME/KEY: 4-bromophenylalanine
<222> LOCATION: (10)..(10)

<400> SEQUENCE: 4

Phe Cys Ala Gly Cys Phe Thr Gly Cys Phe
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)
<220> FEATURE:
<221> NAME/KEY: 4-bromophenylalanine
<222> LOCATION: (10)..(10)

<400> SEQUENCE: 5

Phe Cys Gln Leu Cys Asn Val Leu Cys Phe
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 6

Phe Cys Asp Ile Cys Pro Asn His Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 7

Phe Cys Gln Arg Cys Glu Arg Trp Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: 4-iodophenylalanine
<222> LOCATION: (1)..(1)

<400> SEQUENCE: 8

Phe Cys His Thr Cys Phe Gln Thr Cys
1               5

<210> SEQ ID NO 9
<211> LENGTH: 6
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)
<220> FEATURE:
<221> NAME/KEY: MISC_FEATURE
<222> LOCATION: (4)..(4)
<223> OTHER INFORMATION: Xaa can be Glutamine (Q) or Threonine (T)

<400> SEQUENCE: 9

Tyr Cys Arg Xaa Ser Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)

<400> SEQUENCE: 10

Tyr Cys Arg Thr Ser Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: 3,5-dibromotyrosine
<222> LOCATION: (1)..(1)

<400> SEQUENCE: 11

Tyr Cys Arg Gln Ser Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
<222> LOCATION: (1)..(1)
<220> FEATURE:
<221> NAME/KEY: MISC_FEATURE
<222> LOCATION: (4)..(4)
<223> OTHER INFORMATION: Xaa can be Glutamine (Q) or Threonine (T)

<400> SEQUENCE: 12

Tyr Cys Arg Xaa Ser Cys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
<222> LOCATION: (1)..(1)
```

```
<400> SEQUENCE: 13

Tyr Cys Arg Thr Ser Cys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: mono-iodo tyrosine
<222> LOCATION: (1)..(1)

<400> SEQUENCE: 14

Tyr Cys Arg Gln Ser Cys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 15

Cys Arg Thr Ser Cys
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 16

Cys Arg Gln Ser Cys
1               5
```